United States Patent [19]

Campagna et al.

[11] Patent Number: 5,042,465
[45] Date of Patent: Aug. 27, 1991

[54] METHOD OF IMMOBILIZING A BODY PART WITH AN ORTHOPEDIC CAST

[75] Inventors: Anthony J. Campagna, Roseville, Minn.; Timothy C. Sandvig, Woodville, Wis.; Dean A. Ersfeld, Maplewood; Matthew T. Scholz, Woodbury, both of Minn.

[73] Assignee: Minnesota Mining & Manufacturing Company, St. Paul, Minn.

[21] Appl. No.: 649,715

[22] Filed: Feb. 1, 1991

Related U.S. Application Data

[62] Division of Ser. No. 222,752, Jul. 22, 1988, Pat. No. 4,989,593.

[51] Int. Cl.⁵ .................................................. A61F 5/04
[52] U.S. Cl. ....................................... 128/89 R; 128/90
[58] Field of Search ................... 128/89 R, 90, 91 R, 128/87 R, 89 A, 155, 156

[56] References Cited

U.S. PATENT DOCUMENTS

| | | | |
|---|---|---|---|
| 937,478 | 10/1909 | Sims | 128/91 R |
| 2,947,307 | 8/1960 | Hoppe | 128/90 |
| 3,307,537 | 3/1967 | Simon | 128/90 |
| 3,314,419 | 4/1967 | Quick | 128/90 |
| 3,800,789 | 4/1974 | Schloss | 128/90 |
| 3,826,252 | 7/1974 | Laico | 128/91 R |
| 3,916,887 | 11/1975 | Kelly | 128/851 |
| 3,944,688 | 3/1976 | Inman | 428/90 |
| 3,956,553 | 5/1976 | Palmer | 427/381 |
| 3,990,437 | 11/1976 | Boyden | 128/90 |
| 4,060,075 | 11/1977 | Blomer | 128/90 |
| 4,136,687 | 1/1979 | Dabroski | 128/91 R |
| 4,193,395 | 3/1980 | Gruber | 128/90 |
| 4,204,532 | 5/1980 | Lind et al. | 128/849 |
| 4,235,228 | 11/1980 | Gaylord | 128/91 R |
| 4,273,115 | 6/1981 | Holland | 128/91 R |
| 4,306,549 | 12/1981 | Canie | 128/90 |
| 4,309,990 | 1/1982 | Brooks | 128/90 |
| 4,320,750 | 3/1982 | Dabroski | 128/91 R |
| 4,344,999 | 8/1982 | Gohlke | 128/849 |
| 4,350,246 | 9/1982 | Mayer | 206/210 |
| 4,362,762 | 12/1982 | Lindquist | 128/91 R |
| 4,372,300 | 2/1983 | Drennan | 128/83 |
| 4,411,928 | 10/1983 | Baldwin | 427/2 |
| 4,442,833 | 4/1984 | Dahlen | 128/90 |
| 4,467,013 | 8/1984 | Baldwin | 428/289 |
| 4,618,524 | 10/1986 | Greitasch et al. | 428/198 |
| 4,628,917 | 12/1986 | Campagna | 128/90 |
| 4,657,804 | 4/1987 | Mays | 428/212 |
| 4,667,661 | 5/1987 | Scholz | 128/90 |
| 4,705,712 | 11/1987 | Cashaw | 428/152 |
| 4,725,481 | 2/1988 | Ostapohenko | 428/213 |
| 4,829,992 | 5/1989 | Cilladi | 128/90 |

*Primary Examiner*—Robert A. Hafer
*Assistant Examiner*—Michael Brown
*Attorney, Agent, or Firm*—Wegner, Cantor Mueller & Player

[57] ABSTRACT

A method of immobilizing a body part with an improved orthopedic cast or splint having a padding that has been treated with a fluorochemical or silicone. The padding has an apparent surface tension of less than 60 dynes per centimeter and a porosity of less than about 15 seconds. The padding is able to shed water rapidly, thereby providing more comfort for the user.

11 Claims, 1 Drawing Sheet

METHOD OF IMMOBILIZING A BODY PART WITH AN ORTHOPEDIC CAST

CROSS-REFERENCE TO RELATED APPLICATIONS

This application is a divisional of U.S. Ser. No. 07/222,752, filed July 22, 1988, now U.S. Pat. No. 4,989,593 the disclosure of which is herein incorporated by reference.

BACKGROUND OF THE INVENTION

Casting materials used in orthopedic applications include plaster of paris and variations thereof and curable resin systems. Casts are frequently used in combination with a soft layer of padding applied between the load-bearing casting material and the skin. Most of the plaster of paris and curable resin systems are cured by water or aqueous catalyst systems. Generally this curing is carried out by immersing or otherwise soaking the casting material in water prior to application to the body. This process can result in wetting of the skin and any cast padding used. Furthermore, in use, the cast may be splashed, immersed or otherwise exposed to water, resulting in wetting of the underlying padding. This humid environment can be a breeding ground for microorganisms and can cause serious skin breakdown (maceration). Therefore, if wetted, it is desirable that the cast padding dry as rapidly and completely as possible.

It is desirable to provide a cast padding which dries rapidly if exposed to water. Such a method may permit intentional wetting of the cast, for example during bathing or discretionary exposure to water.

SUMMARY OF THE INVENTION

The present invention provides an orthopedic cast that has a padding which dries more rapidly and more completely than previously available cast padding. The padding is effective even when totally immersed and water is mechanically forced into the air spaces in the padding. The improved chemically treated cast padding of the present invention is obtained by applying to the padding a substantive fluorochemical or silicone compound. Substantive compounds as described herein are those which are not removed from the cast padding under normal usage conditions. The rigidity of the total cast can also be improved by using a chemically-treated, rapidly drying cast padding, particularly when the casting materials are sensitive to water.

DETAILED DESCRIPTION OF THE INVENTION

Figure 1:
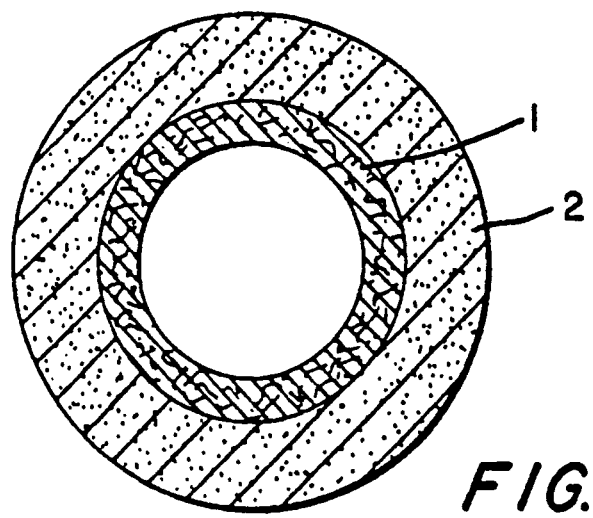
FIG. 1 depicts a cross-sectional view of an orthopedic cast having a padding 1 and a casting material 2.

The present invention relates to an improved orthopedic cast padding that demonstrates rapid drying and water repellency. When cast padding is described herein, any water-permeable porous or microporous knit, woven or nonwoven covering which can be used with the padding material, such as stockinet, is also meant to be included.

Water repellency is imparted to the cast padding by a chemical treatment which provides the elements of the padding such as fibers with a reduced surface energy. It has been found that low surface energy can be provided to the padding from the application of silicones or fluorochemicals. The silicones or fluorochemicals can be applied by solutions, sprays, or plasma vapor to the cast padding material. In addition to having a low surface energy, the cast padding is permeable to air and water vapor and preferably to liquid water.

The cast padding of the present invention can be prepared from any material conventionally used for underpadding with casts. Such padding can be manufactured from cotton, polyester, and other fiber forming materials formed into nonwoven, knit, woven or melt blown constructions. An example of a polyester pad which can be treated by the instant invention is a pad comprised of polyethylene terephthalate, for example polyethylene terephthalate fibers. Foam cast padding can also be treated by the method of the invention.

The fluorochemical or silicone which is added to the padding material to impart low surface energy is generally applied at low levels. Suitable amounts are between 0.001 to 0.10 parts by weight of active ingredient per part of fabric or padding. A preferred range is 0.25 to 2.5 percent by weight, i.e. 0.0025 to 0.025 grams of active ingredient per gram of fabric or padding.

The essential objective of the instant invention is to provide a padding which is treated to possess a low surface energy. In addition to being water repellent, it has surprisingly, been found that water forced into the void spaces could be shed rapidly if the padding possessed a low surface energy. Untreated padding stays soaked for extensive periods of time, resulting in slow and difficult drying even with a heated airstream. The treated padding dries more quickly, shedding the water in the void spaces and retaining much less water in association with the elements of the padding such as fibers.

The method for measuring the surface energy is AATCC Test Method 118-1983, with the modifications described below. Surface energies measured according to this modified test method are hereinafter referred to as "apparent" surface energies.

AATCC test method 118-1983 determines the surface energy of a fabric by evaluating the fabric's resistance to wetting by a series of selected hydrocarbon compositions. The hydrocarbons set forth in AATCC 118-1983, however, only provide for measurements of surface tension from about 19.8 to 27.3 dynes per centimeter at 25° C. This range is extended by employing various mixtures of methanol and water in the fabric resistance test. The compositions and their representative surface tensions are as follows. Surface tensions are taken directly or interpolated from Handbook of Chemistry and Physics, 56th Edition, CRC Press, pp. F-42 and F-43.

| Liquid No. | Composition | Surface Tension (dynes/cm at 25 C.) |
| --- | --- | --- |
| 1 | n-heptane | 19.8 |
| 2 | n-octane | 21.4 |
| 3 | n-decane | 23.5 |
| 4 | n-dodecane | 24.7 |
| 5 | n-tetradecane | 26.4 |
| 6 | n-hexadecane | 27.3 |
| Volume % | | Surface Tension |

-continued

| Liquid No. | Methanol/Water | (dynes/cm at 20 C.) |
| --- | --- | --- |
| 7 | 65/45 | 30 |
| 8 | 53/47 | 35 |
| 9 | 40/60 | 40 |
| 10 | 25/75 | 45 |
| 11 | 21/79 | 50 |
| 12 | 15/85 | 55 |
| 13 | 8.5/91.5 | 60 |
| 14 | 5/95 | 65 |
| 15 | 0/100 | 73 |

The test procedure is as follows. A specimen of the padding is placed flat on a smooth, horizontal surface. The method AATC 118-1983 is used except that beginning with the lowest number test liquid, 5 drops of the liquid are placed on the surface of the fabric in various locations. If three of the five drops wick into the fabric within 60 seconds, the test is reported using the fluid of the next higher surface tension. When at least 3 drops remain on the surface after 60 seconds, the apparent surface energy is the range between the last two liquids used.

A sufficiently low apparent surface energy for the padding has been determined to be less than 60 dynes per centimeter and preferably from 15 to 50 dynes per centimeter. More preferably, the apparent surface energy is 15 to 40 dynes per centimeter, and most preferably 15 to 30.

An advantage of the orthopedic cast or splint of this application is the high porosity which allows the injured limb to breathe. The porosity of the padding is tested using a W & L. E. Gurley Densometer Model 4110 (Troy, N.Y.). A Gurley-Teledyne sensitivity meter (catalogue no. 4134/4135) is used. An Engler Instruments Co. model 605 timer is used to record the time to pass 100 cc of air through a 1.128" diameter (1.000 square inch) a one layer piece of the padding. Thus, porosity is defined in this application and claims as the time it takes 100 cc of air to pass through a one square inch single layer of padding at 74°-76° C. and 50% relative humidity.

Preferably, the padding of this application has a porosity of less than about 15 seconds when measured using a Gurley densometer. More preferably, the padding has a porosity less than about 11 seconds.

Suitable fluorochemicals which can be used to obtain the low surface energy layers of the padding of the instant invention include any of the fluorochemicals known to those skilled in the art to provide water-repellency, and optionally oil repellency to natural or synthetic fibers and films.

In general, fluorochemical agents or compositions useful in this invention comprise fluorochemical compounds or polymers containing fluoroaliphatic radicals or groups, Rf.

The fluoroaliphatic radical, Rf, is a fluorinated, stable, inert, non-polar, preferably saturated, monovalent moiety which is both hydrophobic and oleophobic. It can be straight chain, branched chain, or, if sufficiently large, cyclic, or combinations thereof, such as alkylcycloaliphatic radicals. The skeletal chain in the fluoroaliphatic radical can include catenary divalent oxygen atoms and/or trivalent nitrogen atoms bonded only to carbon atoms. Generally Rf will have 3 to 20 carbon atoms, preferably 6 to about 12 carbon atoms, and will contain about 40 to 78 weight percent, preferably 50 to 78 weight percent, carbon-bound fluorine. The terminal portion of the Rf group has at least one trifluoromethyl group, and preferably has a terminal group of at least three fully fluorinated carbon atoms, e.g., $CF_3CF_2CF_2-$. The preferred Rf groups are fully or substantially fluorinated, as in the case where Rf is perfluroalkyl, $C_nF_{2n+1}-$. Classes of fluorochemical agents or compositions useful in this invention include compounds and polymers containing one or more fluoroaliphatic radicals, Rf. Examples of such compounds include for example fluorochemical urethanes, ureas, esters, amines (and salts thereof), amides, acids (and salts thereof), carbodiimides, guanidines, allophanates, biurets, and compounds containing two or more of these groups, as well as blends of these compounds.

Useful fluorochemical polymers containing Rf radicals include copolymers of fluorochemical acrylate and/or methacrylate monomers with co-polymerizable monomers, including fluorine-containing and fluorine-free monomers, such as methyl methacrylate, butyl acrylate, octadecyl methacrylate, acrylate and methacrylate esters of poly(oxyalkylene) polyol oligomers and polymers, e.g., poly(oxyethylene) glycol dimethacrylate, glycidyl methacrylate, ethylene, vinyl acetate, vinyl chloride, vinylidene chloride, vinylidene fluoride, acrylonitrile, vinyl chloroacetate, isoprene, chloroprene, styrene, butadiene, vinylpyridine, vinyl alkyl esters, vinyl alkyl ketones, acrylic and methacrylic acid, 2-hydroxyethyl acrylate, N-methylolacrylamide, 2-(N,N,N-trimethylammonium)ethyl methacrylate and the like.

The relative amounts of various comonomers which can be used with fluorochemical monomer will generally be selected empirically, and will depend on the substrate to be treated, the properties desired from the fluorochemical treatment, i.e., the degree of oil and/or water repellency desired, and the mode of application to the substrate.

Useful fluorochemical agents or compositions include blends of the various classes of fluorochemical compounds and/or polymers described above. Also, blends of these fluorochemical compounds or polymers with fluorine-free compounds, e.g., N-acyl aziridines, or fluorine-free polymers, e.g., polyacrylates such as poly(methyl methacrylate) and poly(methyl methacrylate-co-decyl acrylate), polysiloxanes and the like.

The fluorochemical agents or compositions can include non-interfering adjuvants such as wetting agents, emulsifiers, solvents (aqueous and organic), dyes, biocides, fillers, catalysts, curing agents and the like.

The final fluorochemical agent or composition should contain, on a solids basis, at least about 5 weight percent, preferably at least about 10 weight percent carbon-bound fluorine in the form of said Rf groups in order to impart the benefits described in this invention.

Such fluorochemicals are generally known and commercially available as perfluoroaliphatic group bearing water/oil repellant agents which contain at least 5 percent by weight of fluorine, preferably 7 to 12 percent of fluorine in the available formulations.

As specifically known formulations, the following examples are named:

By the reaction of the perfluoroaliphatic thioglycols with diisocyanates, there results perfluoroaliphatic group-bearing polyurethanes. These products are normally applied in aqueous dispersion for fiber treatment. Such reaction products are e.g. described in U.S. Pat. No. 4,054,592, incorporated herein by reference.

Another group of suitable compounds are perfluoroaliphatic group-bearing N-methylol condensation products. These compounds are described in U.S. Pat. No. 4,477,498, incorporated herein by reference where the emulsification of such products is dealt with in detail.

The perfluoroaliphatic group-bearing polycarbodimides are, e.g.. obtained by reaction of perfluoroaliphatic sulfonamide alkanols with polyisocyanates in the presence of suitable catalysts. This class of compounds can be used by itself, but often is used with other $R_f$-group bearing compounds, especially with (co)polymers. Thus, another group of compounds which can be used in dispersions is mentioned. Among these compounds all known polymers bearing fluoroaliphatic residues can be used, also condensation polymers, such as polyesters and polyamides which contain the corresponding perfluoroaliphatic groups, are considered but especially (co)polymers on the basis of e.g. $R_f$-acrylates and $R_f$-methacrylates, which can contain different fluorine-free vinyl compounds as comonomers. In DE-A 2 310 801 (see also GB-A 1.413.051/052), these compounds are discussed in detail. The manufacture of $R_f$-group bearing polycarbodimides as well as the combination of these compounds with each other is also described in detail.

Besides the aforementioned perfluoroaliphatic group-bearing agents, further fluorochemical components may be used, for example, $R_f$-group-bearing guanidines, U.S. Pat. No. 4,540,479, $R_f$-group-bearing allophanates, U.S. Pat. No. 4,606,737 and $R_f$-group-bearing biurets, U.S. Pat. No. 4,668,406, the disclosures which are incorporated herein by reference. These classes are mostly used in combination. Others include fluoroalkyl-substituted siloxanes, e.g., $CF_3(CF_2)_6CH_2O(CH_2)_3Si(OC_2H_5)_3$.

The useful compounds show, in general, one or more perfluoroaliphatic residues with preferably at least 4 carbon atoms, especially 6 to 14 atoms each.

An exemplary preferred fluorochemical is a formulation of 70% solvents and 30% emulsified solid fluorochemical polymers. The formulation includes as solvents 11% methyl isobutyl ketone, 6% ethylene glycol and 53% water. The fluorochemical polymers are a 50/50 blend of a 5/95 copolymer of butyl acrylate and

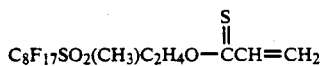

prepared as described in U.S. Pat. No. 3,816,229, incorporated herein by reference (see especially column 3, lines 66–68 and column 4, lines 1–11) for a 10/90 copolymer. The second component of the 50/50 blend is a copolymer prepared from 1 mole of a tri-functional phenyl isocanate (available from Upjohn Company under the name PAPI), 2 moles of $C_8F_{17}N(CH_2CH_3)CH_2CH_2OH$ and 1 mole of stearyl alcohol prepared as described in U.S. Pat. No. 4,401,780, incorporated herein by reference (see especially Table I, C2 under footnote A). Emulsifiers used are conventional commercially available materials such as polyethoxylated quaternary ammonium compounds (available under the name 5% Ethoquad 18/25 from Akzo Chemie America) and 7.5% of a 50/50 mixture of $C_8F_{17}SO_2NHC_3H_6N(CH_3)_3Cl$ and a polyethoxylated sorbitan monooleate (available from ICI Limited under the name Tween 80). Such fluorochemicals are non-yellowing and particularly non-irritating to the skin as well as providing articles that are stable having excellent long-term aging properties.

Exemplary fluorochemicals are available commercially from the Minnesota Mining and Manufacturing Company and include ready to use formulations such as Scotchgard TM Fabric Protectors FC-214 and FC 270, Scotch-Release TM Brand Fabric Treatment FC-248, Scotchgard TM Brand Fabric Protector FC-324, 3M TM Brand Textile Chemical FC-461, 3M TM Brand Textile Chemical FC-210, 3M TM Brand Textile Chemical FC-828, 3M Brand FC 393, FC 326, FC 905 and FC214B, Scotchgard TM Brand Rain and Stain Repeller FC-232 and the like. Other commercially available materials include Soil Shedd TM (available from duPont deNemours and Company, Wilmington, Del.).

Suitable silicones for use to obtain the low surface energy layers of the instant invention include any of the silicones known to those skilled in the art to provide water repellency and optionally oil repellency to fibers and films. Silicone fluids typically consist of linear polymers of rather low molecular weight, namely about 4000-25000. Most commonly the polymers are polydimethylsiloxanes.

For use as fluids with enhanced thermal stability, silicones containing both methyl and phenyl groups are often used. Generally, the phenyl groups make up 10–45% of the total number of substituent groups present. Such silicones are generally obtained by hydrolysis of mixtures of methyl- and phenylchlorosilanes.

Fluids for use in textile treatment may incorporate reactive groups so that theY may be cross-linked to give a permanent finish. Commonly, these fluids contain Si-H bonds (introduced by including methyldichlorosilane in the polymerization system) and cross-linking occurs on heating with alkali.

Examples of suitable silicones are those available from Dow-Corning Corporation such as C2-0563 and from General Electric Corporation such as GE-SS4098.

As shown in the Figures, cast padding 1 is surrounded by or enclosed within, or provided as a protective layer between skin and curable casting material 2. The curable casting material can be any material that is conventionally used as the load-bearing or immobilizing structure in an orthopedic cast. For example, the casting material may consist of a knit, woven or non-woven web or an open-cell foam that is impregnated with a curable composition. The curable composition can be any of the known curable compositions that are used in orthopedic cast applications. Suitable curable compositions include plaster of paris and water-curable, isocyanate functional prepolymers, acrylates, water curable silicone ethers, methacrylates or cyanoacrylate esters, and epoxy resins and vinyl resins. The curable resins include water-cured or heat or light-cured resins. One such suitable casting material is Scotchcast Plus TM brand casting tape, available from 3M Co., St. Paul, Minn.

Figure 2:
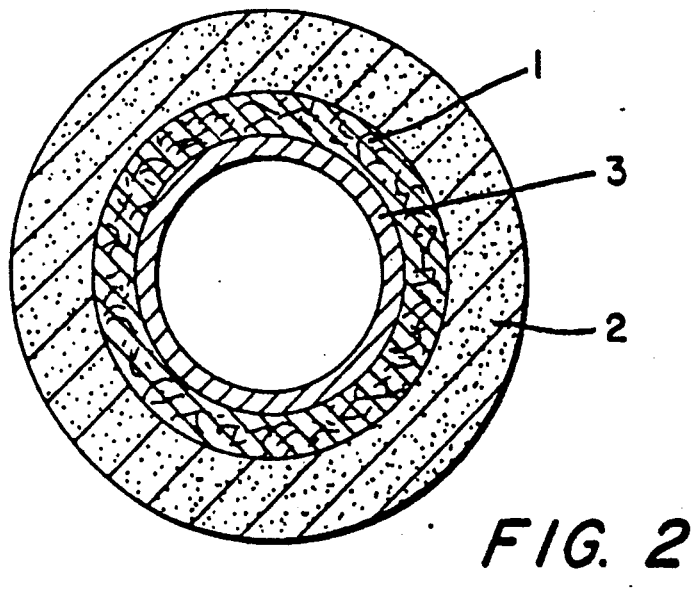
FIG. 2 depicts a cross-sectional view of an orthopedic cast having a padding 1, a casting material 2, and a water-permeable porous or microporous woven, knitted or nonwoven covering 3.

FIG. 2 illustrates an embodiment in which padding 1 is placed or enclosed between casting material 2 and a water-permeable microporous woven or nonwoven covering 3 such as stockinet. When stockinet is used it is usually applied to a limb, then covered with padding.

One method for applying the orthopedic cast of this application to a patient is as follows. First, the cast padding is applied to the area of the patient to be immobilized. Next, the casting material is contacted with an aqueous solution to initiate cure. Finally, the casting material is wrapped around the padding and allowed to cure.

The orthopedic casts of the present invention are safer and more comfortable to the patient during the healing period. In addition, casts made as described and claimed herein are more amenable to various regimens involving hydrotherapy. This allows flexibility in treatment and helps avoid the potential negative side effects associated with the prolonged wetting of the skin.

The following examples are provided to illustrate the invention and should not be construed as limiting it in any way. The scope of the invention is defined by the claims and not by the examples or the description herein.

EXAMPLE 1

Part A. A container of the fluorochemical treatment FC-905 (available from 3M Company, St. Paul, Minn.) at 20 percent solids is diluted with acetone to a 2 percent solids suspension and each of the following materials is submerged and soaked in the suspension for about 15 seconds: (1) A roll of polyester cast padding available from Orthopedic Products Division of the 3M Company, St. Paul, Minn. as MSO4, (2) a roll of polyethylene terephthalate stockinet available from Orthopedic Products Division of 3M Company, St. Paul, Minn. as MSO2. The rolls are then squeezed to remove excess liquid and oven dried at 49 0OU0p10h12v0s0b3T Part B. The fluorochemical treatment is changed to FC-326 at 40% solids content, which is diluted with acetone to obtain a 2 percent solids solution and the rolls are soaked and dried. The same procedure employed in part A is used.

Part C. Fluorochemical treated test samples are made from a rectangular flattened cylinder of 7.6 cm by 5.1 cm (3 in by 2 in) (about 1 mm thickness per layer of treated stockinet) and two 7.6 cm by 10.2 cm (3 in by 4 in) rectangular wraps of the treated cast padding from Parts A and B by covering the stockinet with a layer of the padding and rolling the laminate into a cylinder with the padding as the outside layer. Untreated test samples are made in the same way. The extent of wetting of the cigar-shaped cylindrical test samples is determined by measuring the dry weight of each sample, then soaking each sample by one of two methods: (1) passively by holding them under water for about 15 seconds followed by shaking each three times to remove excess water, or (2) actively by soaking each sample by holding them under water for about 15 seconds accompanied by five pumps of the hand to mechanically pump additional water into the void spaces, followed by shaking each sample three times to remove excess water. The moist weight of each test sample is then measured immediately. Results are shown in Table 1.

TABLE 1

| Sample | Dry Weight (grams) | Average Weight (Grams) Passive Soaked | Percent Increase | Average Weight (Gram) Active Soak | Average Percent Increase |
|---|---|---|---|---|---|
| Untreated | 2.92 | 12.0 | 311 | 11.9 | 309 |
| FC-326 Treated | 2.90 | 3.3 | 13 | 5.1 | 77 |
| FC-905 Treated | 2.80 | 3.1 | 11 | 5.1 | 81 |

This experiment clearly shows that the treated pads retained much less water after either active or passive soaking.

EXAMPLE 2

In order to evaluate the use of a cast padding of the invention, three types of cast padding are treated as follows: Various fluorochemical textile treatment solutions are diluted to 4% solids with acetone (or in the case of FC-214 the solvent is water). The various padding materials are soaked in the fluorochemical solution for two or three minutes. The excess solution is squeezed out and the padding material is dried in a 49° C. oven overnight in the case of FC-326 and FC-905, and in a 149° C. oven for 20 minutes in the case of FC-214. The materials prepared are described in Table 2.

TABLE 2

| Padding Treated | Fluorochemical Treatments | | | Porosity (sec) |
|---|---|---|---|---|
| 4 inch wide synthetic cast padding (3M Co., St. Paul, MN) | FC-326 4% solids | FC-214 2.1% solids | FC-905 4% solids | 0.2 |
| 5 ft long, 2 inch wide stockinet (knit polyester) (3M Co., St. Paul, MN) | FC-326 4% solids | FC-214 2.1% solids | FC-905 4% solids | 0.2 |
| 9 inch long orlon tube of 6.4 cm (2.5 in) diameter terry cushion stockinet no. 82025 (Balfour Corp.) | FC-326 4% solids | FC-214 2.1% solids | FC-905 4% solids | 1.1 |
| Orlon padding of 10.2 cm (4 inch) | FC-326 4% solids | FC-214 2.1% solids | None | 1.6 |

Volunteers in a blind test wear a treated padding and stockinet on one arm and an untreated padding and stockinet on the other arm. Each padding is covered by a cast of one roll of 3 inch wide Scotchcast. Plus brand casting tape activated by dipping in water and wrapping over the padding and stockinet on each arm.

After the casting material is cured (15 to 30 minutes) each volunteer dips both arms into a container of water allowing water to penetrate the cast and run under the cast from both ends. All volunteers report that the water drains from the treated side faster than it drains from the untreated side. Each volunteer continues normal activity, including showers, throughout a 24 hour period. Each cast and padding is then removed, weighed and dried in an oven at 66° C. overnight, then weighed again to determine water remaining. Water loss is calculated. The results are shown in Table 3.

TABLE 3

| Padding Treatment | Weight After Removal (Grams) | Weight After Dried (Grams) | Net Water Loss (Grams) |
|---|---|---|---|
| Synthetic Cast Padding and Stockinet | | | |
| 2.1% FC 214 | 146.93 | 145.47 | 1.48 |
| Untreated Control | 148.57 | 144.45 | 4.12 |
| 4% FC 326 | 160.04 | 152.60 | 7.44 |

TABLE 3-continued

| Padding Treatment | Weight After Removal (Grams) | Weight After Dried (Grams) | Net Water Loss (Grams) |
| --- | --- | --- | --- |
| Untreated Control Orlon Tubular Material: | 156.04 | 132.84 | 23.20 |
| 4% FC 326 | 135.82 | 131.38 | 4.44 |
| Untreated Control | 172.02 | 129.90 | 42.12 |
| 4% FC 905 | 161.00 | 155.57 | 5.49 |
| Untreated Control | 188.58 | 161.80 | 26.78 |
| 2.1% FC 214 | 192.22 | 167.30 | 24.92 |
| Untreated Control | 219.50 | 169.00 | 50.50 |

All volunteers report the treated side dries much faster, is more comfortable and causes less itching.

It was observed that the casts covering treated padding and stockinet were more rigid than the casts covering untreated padding and stockinet when the casts were removed.

What is claimed is:

1. A method of immobilizing a body part comprising the steps of (a) applying a padding to the body part such that a surface of the padding covers the body part and an opposing surface is exposed, (b) applying an activated, curable casting material to the exposed surface of the padding, and (c) allowing the material to cure, wherein the padding is treated with a fluorochemical or silicone and has an apparent surface energy less than about 60 dynes per centimeter and a porosity of less than about 15 seconds.

2. The method of claim 1 wherein the padding has an apparent surface energy less than about 30 dynes per centimeter.

3. The method of claim 1 wherein the padding is treated with a silicone.

4. The method of claim 1 wherein the padding is treated with a fluorochemical.

5. The method of claim 4 wherein the fluorochemical comprises an emulsified fluorochemical polymer in a solvent.

6. The method of claim 1 wherein the fluorochemical or silicone is present in amounts between 0.01 to 10% by weight of the padding.

7. The method of claim 1 wherein the fluorochemical or silicone is present in amounts between 0.25 and 2.5% by weight of the padding.

8. The method of claim 1 wherein the padding is cotton, polyester, or foam.

9. The method of claim 1 wherein the activated, curable casting material comprises a web that is impregnated with a water-curable compound and soaked in water.

10. The method of claim 9 wherein the curable compound is a polyurethane prepolymer.

11. The method of claim 10 wherein the curable compound is plaster of paris.

* * * * *